United States Patent [19]

Igaki

[11] Patent Number: 5,762,625
[45] Date of Patent: Jun. 9, 1998

[54] LUMINAL STENT AND DEVICE FOR INSERTING LUMINAL STENT

[75] Inventor: Keiji Igaki, Shiga, Japan

[73] Assignee: Kabushikikaisha Igaki Iryo Sekkei, Shiga, Japan

[21] Appl. No.: 232,181

[22] PCT Filed: Sep. 8, 1993

[86] PCT No.: PCT/JP93/01277

§ 371 Date: May 3, 1994

§ 102(e) Date: May 3, 1994

[87] PCT Pub. No.: WO94/05364

PCT Pub. Date: Mar. 17, 1994

[30] Foreign Application Priority Data

Sep. 8, 1992 [JP] Japan ..................... 4-239849

[51] Int. Cl.⁶ .................. A61F 2/06; A61M 29/02
[52] U.S. Cl. .................. 604/8; 528/370; 606/192
[58] Field of Search .................. 606/192–198, 606/228–231; 604/8, 93, 154, 208, 228; 623/1, 15, 16, 12

[56] References Cited

U.S. PATENT DOCUMENTS

| | | | |
|---|---|---|---|
| 4,045,418 | 8/1977 | Sinclair | 260/78.3 |
| 4,922,905 | 5/1990 | Strecker | 606/195 |
| 4,950,227 | 8/1990 | Savin et al. | 604/8 |
| 5,059,211 | 10/1991 | Stack et al. | 606/198 |
| 5,085,629 | 2/1992 | Goldberg et al. | 604/8 |
| 5,147,399 | 9/1992 | Dellon et al. | 623/12 |
| 5,195,984 | 3/1993 | Schatz | 606/195 |
| 5,274,074 | 12/1993 | Tang et al. | 528/370 |

FOREIGN PATENT DOCUMENTS

| | | |
|---|---|---|
| 2 025 626 | 3/1991 | Canada. |
| 0 183 372 A1 | 6/1986 | European Pat. Off.. |
| 0 282 175 A1 | 9/1988 | European Pat. Off.. |
| 0 326 426 A2 | 8/1989 | European Pat. Off.. |
| 0 441 516 A3 | 8/1991 | European Pat. Off.. |
| U-9 014 845 | 2/1991 | Germany. |
| 54-151675 | 11/1979 | Japan. |
| 60-158858 | 8/1985 | Japan. |
| 1-126962 | 5/1989 | Japan. |
| 2-167156 | 6/1990 | Japan. |
| 3-21262 | 1/1991 | Japan. |
| WO 90/01969 | 3/1990 | WIPO. |
| WO 90/04982 | 5/1990 | WIPO. |
| WO 91/12779 | 9/1991 | WIPO. |
| WO 91/17789 | 11/1991 | WIPO. |
| WO 93/06792 | 4/1993 | WIPO. |
| WO 93/15787 | 8/1993 | WIPO. |

OTHER PUBLICATIONS

Abstracts of 63rd Scientific Session, III–72, Supplemental III Circulation, vol. 82, No. 4, Oct. 1990.

*Primary Examiner*—Michael Buiz
*Assistant Examiner*—Nancy Mulcare
*Attorney, Agent, or Firm*—Limbach & Limbach

[57] ABSTRACT

A luminal stent inserted and fixed in a vessel, such as a blood vessel, so as to maintain the shape of the vessel, and a device for inserting and fixing the luminal stent, are disclosed. The luminal stent is formed of a yarn of bioabsorbable polymer fibers, which yarn is shaped in a non-woven non-knitted state in, for example, a meandering state, around the peripheral surface of an imaginary tubular member. The bioabsorbable polymer includes polylactic acid, polyglycol acid, polyglactin, polydioxanone, polyglyconate, polyglycol acid and a polylactic acid-ε-caprolactone copolymer. The device for inserting and fixing the luminal stent consists in a catheter having a balloon-forming portion in the vicinity of a distal end thereof and the luminal stent fitted on the balloon-forming portion and affixed to the balloon-forming portion by a bio-compatible material, such as an in vivo decomposable polymer, such as polylactic acid, water-soluble protein or fibrin sizing agent.

11 Claims, 8 Drawing Sheets

1
LUMINAL STENT AND DEVICE FOR INSERTING LUMINAL STENT

TECHNICAL FIELD

This invention relates to a luminal stent adapted to be inserted into the vessel, such as a blood vessel, lymph vessel, bile duct vessel, ureter vessel or esophagus for maintaining the shape of the vessel. More particularly, it relates to a luminal stent inserting device for inserting the luminal stent to a desired site in the vessel.

BACKGROUND ART

As this type of the luminal stent, there is known a textile structure in which linear longitudinal and transversal materials of stainless steel or the like are woven or knitted in a tube, and which may be enlarged and fitted to a site of an vasculogenetic operation.

However, this known type of the luminal stent suffers from the problem that it is harder and likely to apply the stress to the vessel to produce inflammation or excess hypertrophy susceptible to re-constriction in the vessel, and that the stent is left semi-permanently as a foreign matter in the living body which by nature acts to dispel such foreign matter.

If the luminal stent, such as a metal stent, which is left in the vessel semi-permanently or for a period longer than is necessary, is inserted into the vessel, it tends to act as a kind of a nucleus around which re-constriction is likely to occur in the vessel. In addition, if a part of the vessel in the vicinity of the stent is injured, there is a risk that the cells on the inner wall of the vessel increase in number due to multiplication to reduce the inner diameter of the vessel.

DISCLOSURE OF THE INVENTION

It is an object of the present invention to provide a luminal stent which is less susceptible to re-constriction in the vessel or reduction in the inner vessel diameter, and a device for inserting the luminal stent.

That is, the present invention is characterized in that a yarn formed of a continuous bioabsorbable polymer fibers is formed in a non-woven, non-knitted state in a shape conforming to the peripheral surface of an imaginary tubular member. Such a luminal stent is fitted on a balloon-forming portion in the vicinity of the distal end of a catheter and bonded to the balloon-forming portion by means of a bio-compatible material which does not cause any rejection symptoms.

The present invention includes a tubular luminal stent prepared in such a manner that the yarn formed of a continuous bioabsorbable polymer fibers is formed in a non-woven non-knitted state in a shape conforming to the peripheral surface of an imaginary tubular member. The stent prepared in this manner is superior in pliability and shape retentivity to other cloths, that is, non-woven fabrics like felt or a customary woven cloth prepared from weft and warp yarns. The knitted luminal stent may be further improved in pliability and shape retentivity by heat treatment (heat-setting).

The above-mentioned luminal stent is inserted into the site of vasculogenesis via a catheter provided with a balloon. If, after the luminal stent is fitted on the balloon-forming portion, the solution of the bioabsorbable polymer is applied for bonding the luminal stent to the balloon-forming portion, the luminal stent may be prevented from being deviated in its position at the time of insertion of the catheter into the vessel.

With the above-described luminal stent of the present invention, the inflammation or excess hypertrophy of the vessel is not produced and hence re-constriction may be prevented from occurring. Also, the luminal stent disappears in several months by being absorbed into the living tissue and is therefore convenient for the living body.

In addition, with the device for inserting and fixing the luminal stent of the present invention, since the luminal stent is immobilized in the balloon-forming portion, the luminal stent may be reliably inserted and fixed in the vessel.

BEST MODE FOR CARRYING OUT THE INVENTION

The present invention is concerned with a luminal stent comprising a tubular body of the yarn of the bioabsorbable polymer fibers, and a luminal stent inserting device in which the stent is applied over a balloon-forming portion of a catheter.

The bioabsorbable polymers include polylactic acid (PLA), polyglycol acid (PGA), polyglactin (polyglycol acid—polylactic acid copolymer), polydioxanone, polyglyconate (trimethylene carbonate—glycolide copolymer), and a copolymer of ε-caprolactone with polyglycol acid or polylactic acid.

A variety of materials, including pharmaceuticals, may be mixed into the bioabsorbable polymer. These materials may also be affixed to the fiber surface.

The luminal stent of the present invention is inserted into the site of vasculogenesis via a catheter fitted with a balloon and is mounted in place by being extended as a result of inflation of the balloon. Although the shape of the luminal stent thus inserted is maintained for several weeks to several months after the insertion, it is formed of the bioabsorbable polymer fibers and hence disappears by being absorbed into the living tissue after the lapse of several months after the insertion.

In addition, if a material impermeable to X-rays is mixed into the bioabsorbable polymer, the state of the luminal stent may be recognized on irradiation of X-rays from outside after its insertion.

The luminal stent of the present invention essentially consists of a single yarn entwined around the peripheral surface of a tubular member into a tubular form without weaving or knitting the yarn. Although the yarn is entwined around the peripheral surface of the tubular member, it is not in the wound or coiled state around the tubular member. That is, the yarn of the bioabsorbable polymer fibers is meandered or coiled into one or more loops, as shown in FIGS. 1a to 1g, for forming a planar yarn mass formed by meandered and/or coiled bioabsorbable polymer fibers, which yarn mass is entwined around the tubular member for producing a fiber mass extending along a curved surface.

Figure 1:
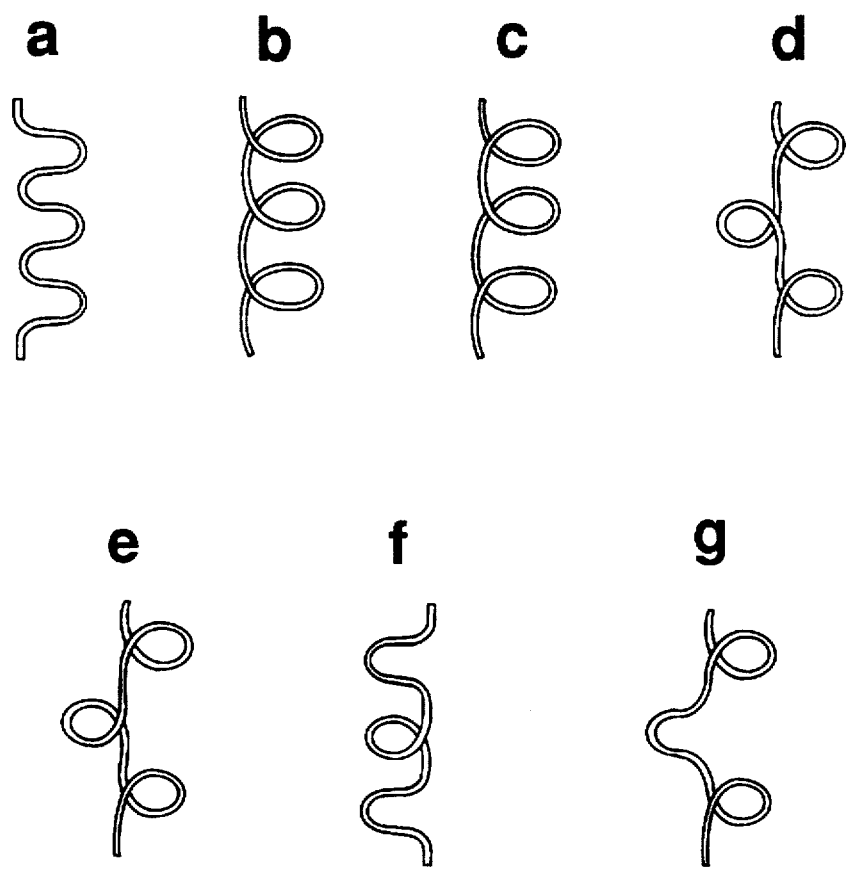
FIG. 1 is a schematic view showing several morphological examples of bioabsorbable polymer fibers in the non-woven non-knitted state.
Figure 2:
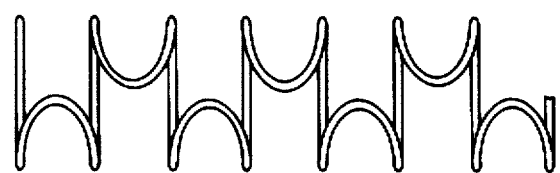
FIG. 2 is a schematic side view showing an example of a luminal stent to which the present invention is applied.
Figure 3:
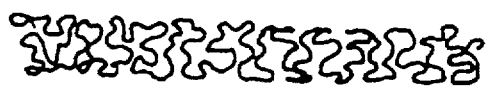
FIG. 3 is a schematic side view showing another example of a luminal stent to which the present invention is applied.

FIG. 2 shows an example of a luminal stent according to the present invention in which a meandering yarn formed of bioabsorbable polymer fibers is shaped into a tube. FIG. 3 shows another example of a luminal stent according to the present invention in which a looped yarn formed of bioabsorbable polymer fibers is similarly shaped into a tube.

When transporting the luminal stent of the present invention to a target site, it can be passed through various meandering vessels substantially more easily than the metal stent or the woven or knitted textile stent. That is, the luminal stent prepared from the yarn formed of bioabsorbable polymer fibers is able to follow any meandering path with excellent trackability, while it can be inserted as far as and fixed at a bent site because the yarn formed into a tubular shape by meandering without being woven or knitted exhibits strong extendibility and is not likely to injure the cavity. According to the present invention, in order for the luminal stent in the shape of a tube about 5 mm in diameter to be introduced into a vessel of the living body which is lesser in diameter, the tube is heat-set by heat treatment and thereby shrunk to a diameter of approximately 2 mm or less. The process is illustrated in FIG. 4.

The heat-set luminal stent is inserted into the vessel in the manner shown in FIG. 5, as will be explained subsequently.

Figure 6:
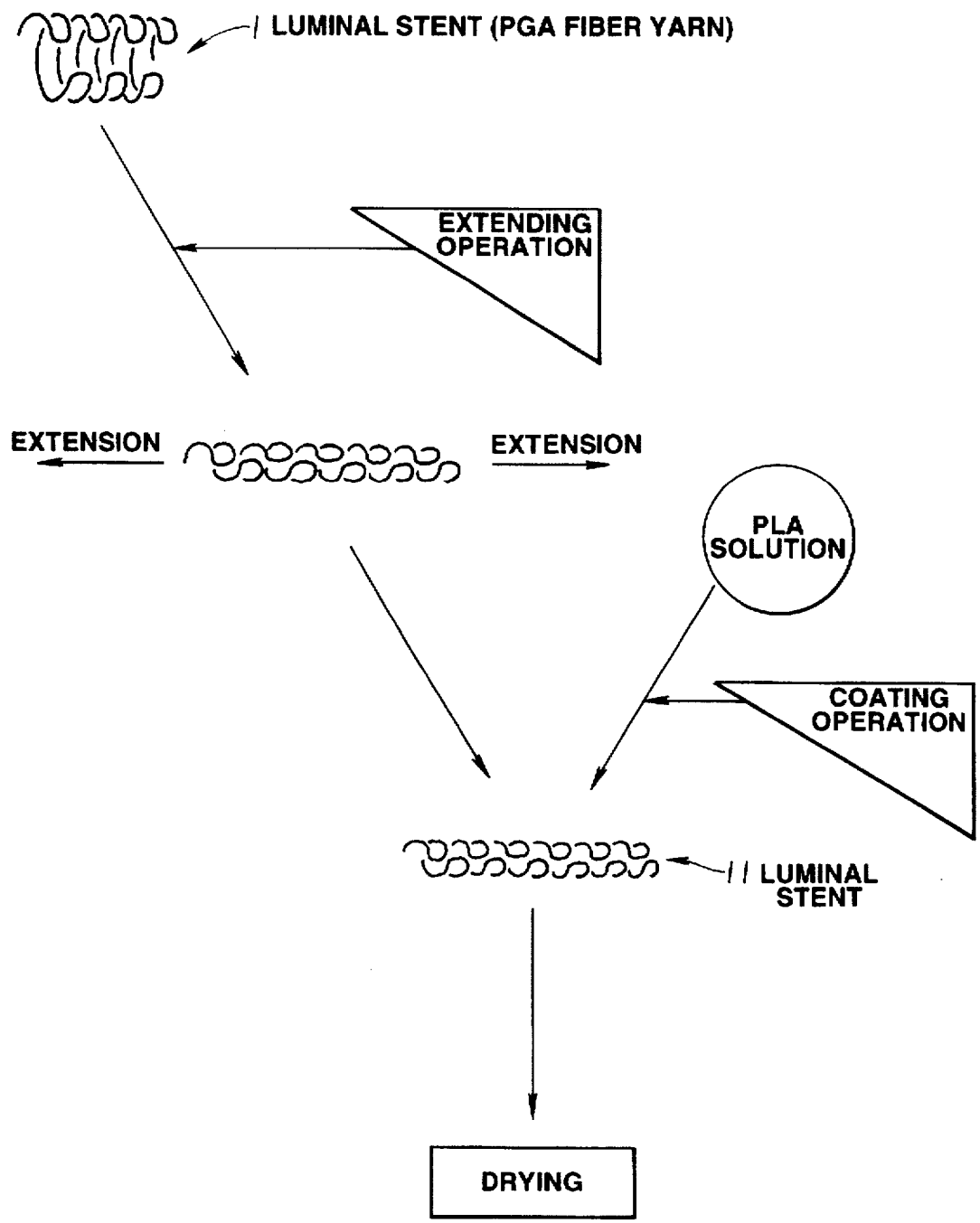
FIG. 6 illustrates an alternative method for reducing the diameter of a luminal stent knitted with the yarn formed of PGA fibers.

FIG. 6 shows another method of contracting the diameter of a luminal stent formed by shaping the yarn of PGA (polyglycol acid) polymer fibers. The method shown in FIG. 6 has an advantage in that, since a tube formed of a heat-resistant resin or metal is not employed, the stent may be directly introduced into and fixed at a balloon forming area in the vicinity of a foremost part of a catheter.

Figure 4:
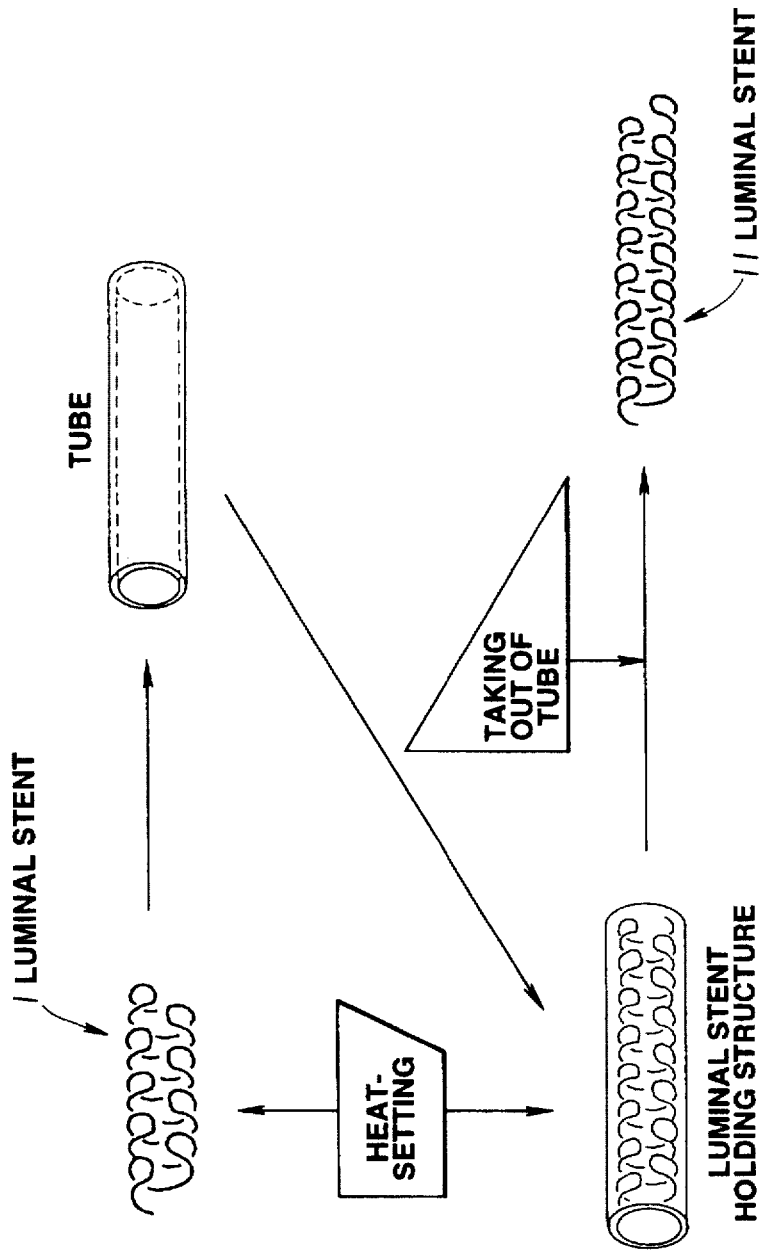
FIG. 4 illustrates the process of producing a luminal stent.

The tubular luminal stent prepared by shaping a yarn of bioabsorbable polymer fibers has a diameter of approximately 4 to 5 mm and is heat-set by being housed in or gradually introduced into a tube of a heat-resistant resin or metal having an inner diameter of 1 to 3 mm and preferably 2 mm for producing a luminal stent having a diameter of approximately 2 mm, as shown in FIG. 4.

In addition, the tubular luminal stent may be heat-set while in the larger diameter. Alternatively, the tubular luminal stent may be reduced in diameter and heat-set for maintaining good shaping properties. The heat setting not only is effective for maintaining the shape of the luminal stent but is meaningful in minimizing the stress applied to the inner wall of the vessel of the living body.

Meanwhile, by forming the bioabsorbable polymer fibers of PLA and PGA, and changing their mixing ratio, the time period required for the strength of the luminal stent of the present invention to be decreased to one-half of the original strength, or the time period until extinction of the luminal stent through absorption into the living body, may be freely controlled within a range from three weeks to three months.

If an agent impermeable to X-rays is mixed into the fibers at the time of spinning the fibers into a yarn, the state of insertion of the luminal stent can be observed by the X-rays. Thrombolytic agents or anti-thrombotic agents, such as heparin, urokinase or t-PA, may also be mixed for optimum effects.

Furthermore, since the luminal stent of the present invention is formed of the yarn of bioabsorbable polymer fibers, and hence it disappears from the site of vasculogenesis in a preset period, carcinostatic agents or various other pharmaceutical may be mixed into or affixed on the fibers for concentrated administration of the pharmaceutical to the site of lesion.

In addition, the fibers making up the luminal stent of the present invention may be variegated in the cross-sectional shape thereof more easily than in the case of preparing the luminal stent of metal. That is, by setting the cross-sectional shape of the filaments on spinning so as to be of a hollow or profiled shape, such as an elliptical or a flower petal shape, or by employing monofilaments or multifilaments, it becomes possible to control bio-compatibility or shape retention characteristics.

The yarn formed of a synthetic high molecular material may have its fiber surface processed in desired manner. With the yarn having the usual substantially circular cross-section and having its surface not processed in any particular manner, the yarn having the so-called profiled cross-section, or the yarn processed as described above, it becomes possible to deposit an anti-thrombotic material or a thrombolytic agent on the yarn or cells of the living body to promote multiplication of the endothelial cells of the living body or to deposit a material impermeable to X-rays. In this case, longitudinally extending flutes or a variety of recesses may be formed on the yarn surface for improving the deposition efficiency.

If it is desired to increase the diameter of a constricted portion of the vessel to a diameter of, for example, 4 mm and to maintain this diameter, it is not increased at a time. That is, for avoiding the sudden stress being applied to the vessel and to the living body, the vessel is expanded initially to a diameter of 3 mm, using an expander having a balloon-forming portion having a diameter of approximately 0.8 to 1.2 mm, after which the catheter provided with a balloon is extracted. A catheter provided with a balloon, which catheter is not fitted with a luminal stent and is capable of only forming a balloon, is again inserted for enlarging the vessel to a diameter slightly larger than 4 mm. Subsequently, a knitted luminal stent is introduced and fixed at the balloon forming portion using a device for inserting and fixing the luminal stent of the present invention.

It is unnecessary to expand and form the vessel stepwise. Thus, it is possible to expand the constricted portion of the vessel at a time to a desired diameter and subsequently proceed to the fitting of the luminal stent.

On the other hand, the luminal stent fitting device itself, consisting in a catheter fitted with a balloon and a luminal stent of the present invention fitted thereon, may be used for inserting and fixing the luminal stent in the vessel of the living body simultaneously with expansion of the vessel.

The device for inserting and fixing the luminal stent of the present invention in a constricted portion of the vessel of the living body is explained in detail. There is an area 3 in the vicinity of the distal end of a catheter 2 in which a balloon of a desired diameter may be formed by the liquid or the gas, such as an X-ray contrast medium, which is injected from a hollow portion in the catheter at a liquid pressure of 8 to 10 atmospheres, as shown in FIG. 5. It is over this balloon-forming area 3, which is about 20 mm long, that a luminal stent 11 about 2 mm in diameter, as heat-set, is applied.

It is noted that the length of the balloon-forming area 3 or the diameter of the luminal stent 11 may be optionally set depending on the type of the vessel to be treated or the specific properties of the vessel.

Meanwhile, a guide wire acting as a leading wire when inserting the catheter into the vessel of a living body is sometimes mounted on the distal end of the catheter.

As for the insertion of the luminal stent, a mid part along the length of the balloon-forming area of the catheter is formed with a communication orifice via which the fluid injected for balloon formation is caused to flow out at the mid portion of the catheter so as to be charged into a space between it and a thin film forming the balloon. It is via this orifice that the balloon is formed under a fluid pressure of 8 to 10 atmospheres, with the ballooned state being kept for 30 to 60 seconds and occasionally for a longer time duration. At this time, the balloon undergoes a kind of plastic deformation and is maintained under the inflated condition under the inflating pressure exerted by the balloon. The inflated shape is maintained by changes in the polymer itself on the molecular level or the yarn shaped into a tube is expanded in the radial direction for maintaining the expanded shape.

Figure 5:
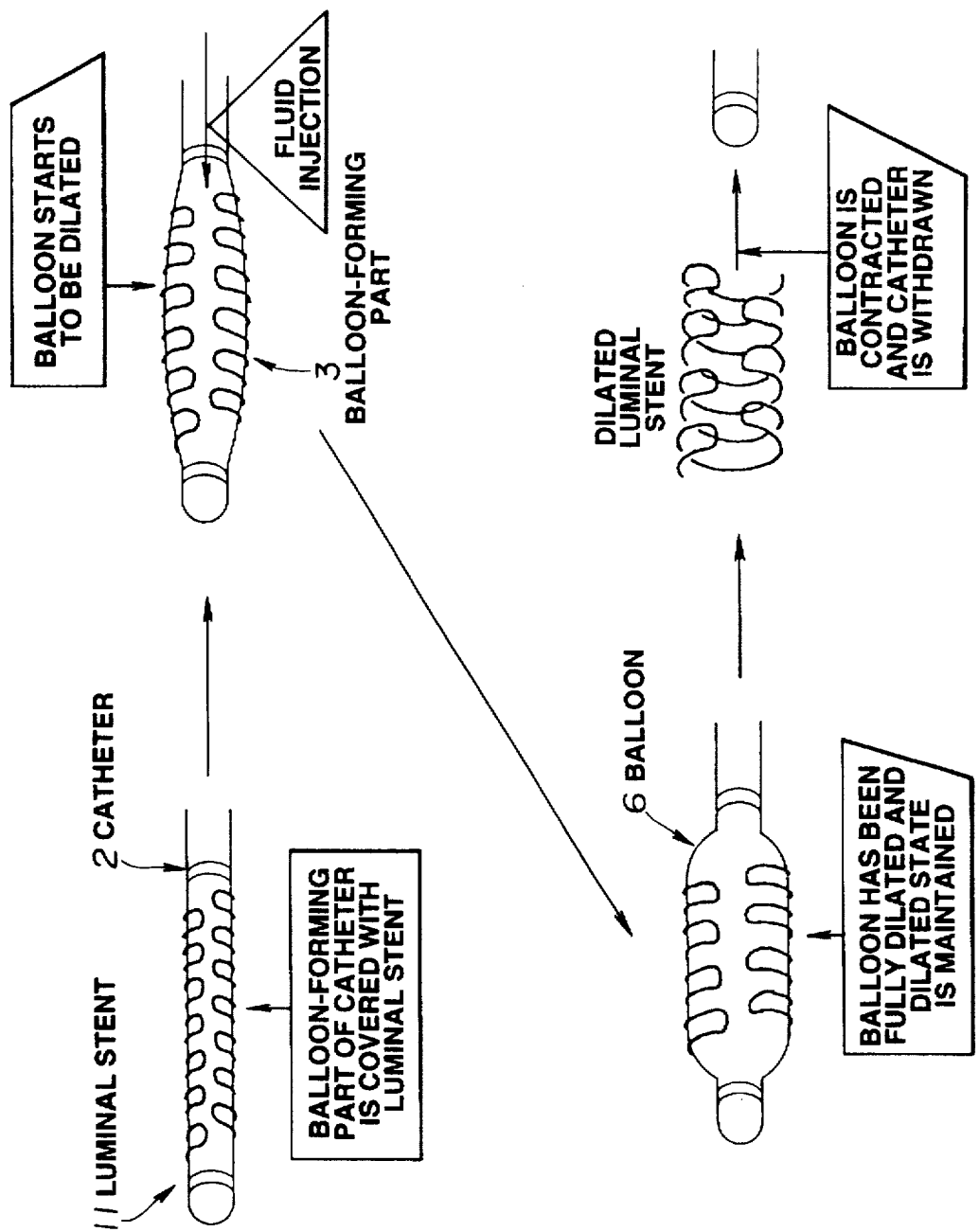
FIG. 5 illustrates the process of inserting and placing the luminal stent in place within in the vessel.

FIG. 5 shows the process of inserting and fitting the luminal stent of the present invention in the vessel of a living body. As shown therein, the balloon is inflated and subsequently contracted to permit the catheter 2 in its entirety to be withdrawn from the luminal stent.

Figure 7:
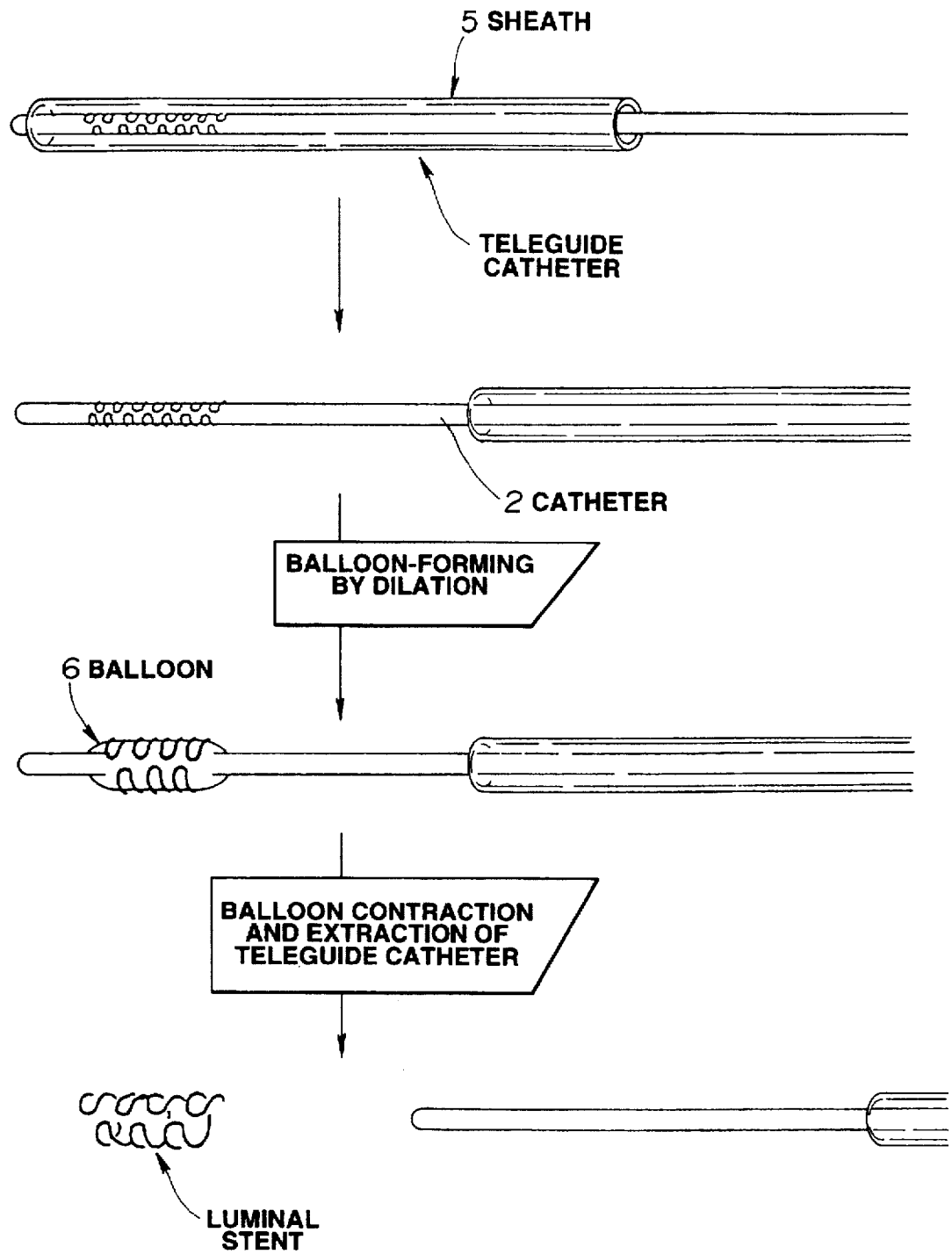
FIG. 7 shows another example of a device for inserting a luminal stent formed of knitted goods.

FIG. 7 shows another embodiment of a luminal stent inserting and fitting device according to the present invention. A catheter fitted with a balloon, on which the luminal stent 11 is subsequently wrapped, is encased within a sheath 5. The resulting assembly is inserted into the vessel of the living body. The sheath is extracted slightly and the balloon is inflated and maintained in the inflated state. The balloon is contracted and the sheath 5 is extracted along with the catheter 2 so that the luminal stent is left in the vessel of the living body.

Meanwhile, the film for balloon formation may be formed of any of a variety of synthetic high molecular materials, such as polyethylene terephthalate or polyethylene.

Figure 8:
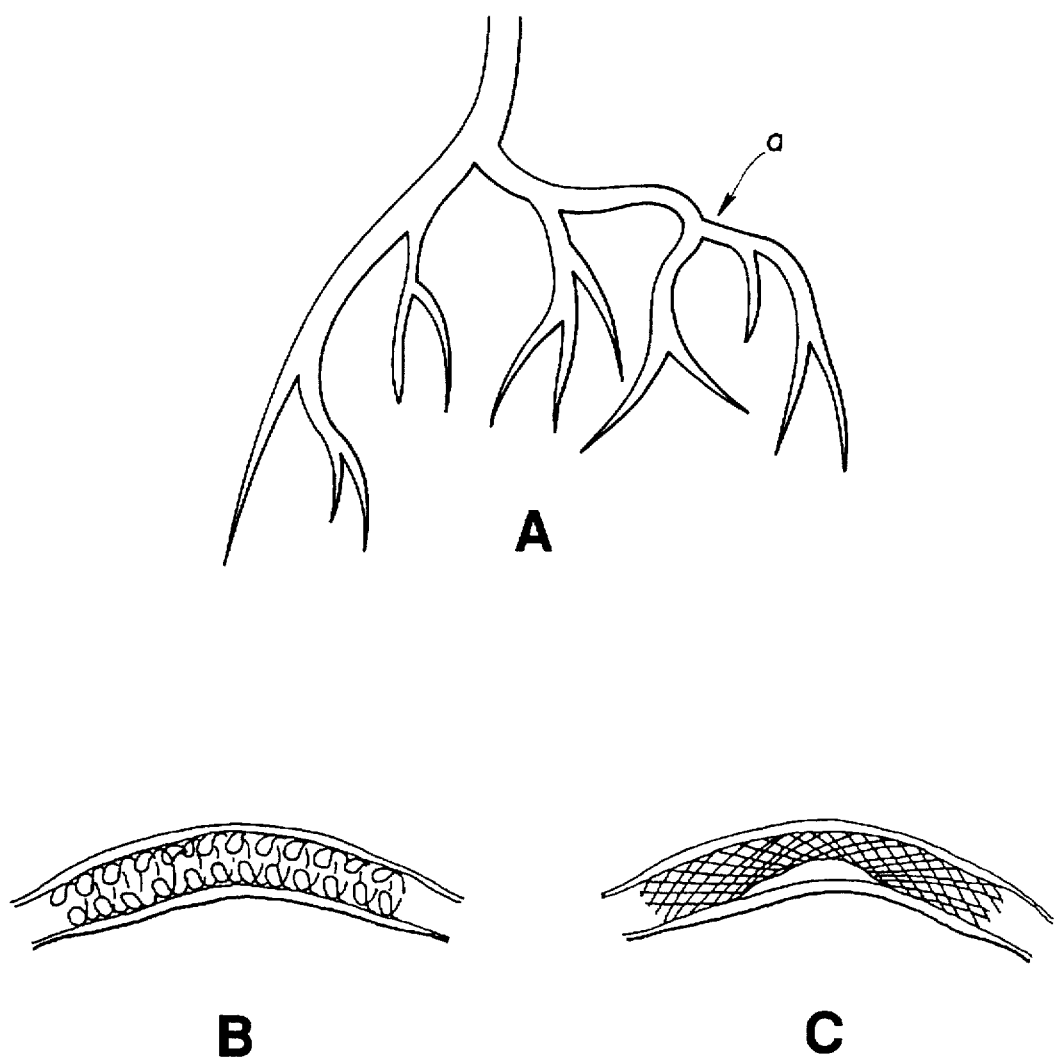
FIG. 8 schematically illustrates a vessel and the state of insertion of the luminal stent, where A shows the morphology of an exemplary vessel, B shows the state of insertion of the luminal stent, and C shows, as a comparative example, the state of poor insertion of a conventional luminal stent.

It is noted that the luminal stent of the present invention may be inserted and fitted in a bend of the vessel to conform to its shape, as shown in FIG. 8. The state of the stent as inserted and fitted is shown in FIG. 8B. A metal stent formed of a woven or knitted textile of linear longitudinal and transverse materials and subsequently formed into a tubular form is shown in FIG. 8C in the state of being inserted into and fitted in a bend of the vessel. Such stent is flexed in the bend of the vessel so that the normal shape of the vessel cannot be maintained at the site. Conversely, the luminal stent of the present invention is able to follow a branched section in the vessel with good trackability so that it can reach any constricted site in the vessel, as discussed previously.

In FIG. 8A, showing a typical shape of the vessel of a living body, the site shown by an arrow a represents a site assumed to be the mounting site for the luminal stent of the present invention.

Figure 9:
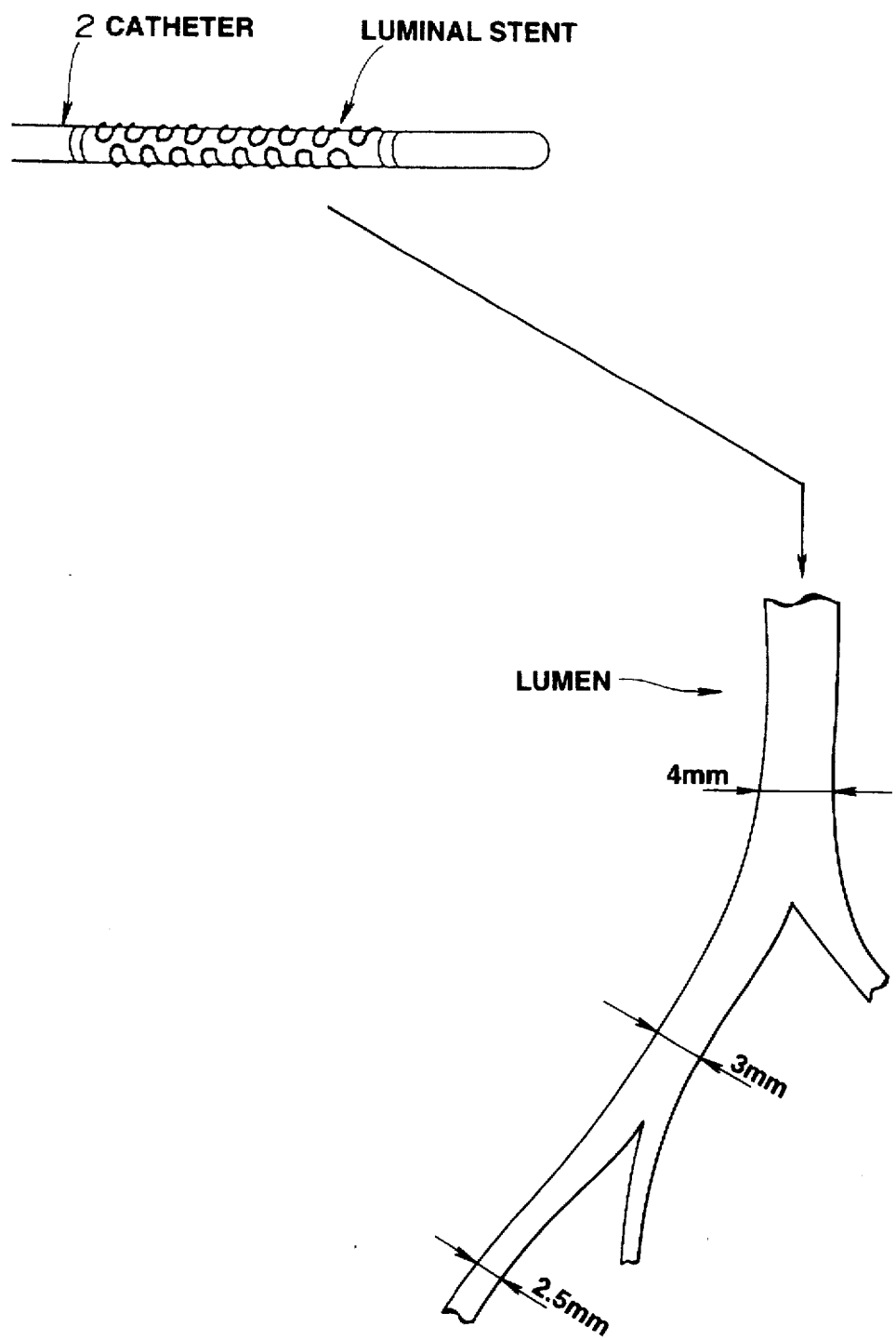
FIG. 9 illustrates that the luminal stent can be inserted into and placed at various sites within the vessel.

The luminal stent of the present invention, as formed by the yarn of the bioabsorbable polymer fibers and heat-set, may be adapted to a vessel of an arbitrary thickness by means of the luminal stent inserting and fixing device according to the present invention. If it is assumed that the luminal stent is applied to a site where the vessel is enlarged to a diameter of approximately 4 mm or larger on inflation of the balloon, the luminal stent may be applied to the vessel site having the diameter of 2.5 mm by controlling the degree of inflation of the balloon. The luminal stent may similarly be applied to a vessel site having the diameter of 3 to 4 mm. That is, the luminal stent may be applied to any site shown in FIG. 9 using the same catheter provided with the balloon. The reason is that the inner diameter of the luminal stent may be maintained at a diameter corresponding to the diameter of the inflated balloon.

If vessel re-constriction is produced in several months after the luminal stent of the present invention is decomposed and absorbed to the living body, the luminal stent may be applied again to the same site because the stent is formed of biodegradable and absorbable polymer material.

The luminal stent of the present invention, as described above, is not susceptible to inflammation or excess hypertrophy of the vessel, and hence the re-constriction may be prevented from occurrence. In addition, the luminal stent is compatible with the living body because it vanishes in several months by being absorbed by the living tissue.

If an agent impermeable to X-rays is applied to the bioabsorbable polymer fibers or the yarn, the state of insertion of the luminal stent may be checked easily by irradiation of X-rays from outside.

Also, the luminal stent may be applied on the balloon-forming portion of the catheter provided with the balloon according to the present invention for inserting and fitting the stent at any desired location in the vessel.

Meanwhile, if the luminal stent of the present invention is applied over the balloon-forming portion of the catheter fitted with the balloon for fixing the stent at a desired site in the vessel, it may occur that the fixing position of the luminal stent is deviated due to contact of the stent with the inner wall of the vessel. If the luminal stent is deviated in its position and disengaged from the balloon forming region, it becomes difficult to realize an optimum expanded position.

Thus it is desirable to apply a bio-compatible material on the luminal stent applied over the balloon-forming region by way of "sizing" for immobilizing the luminal stent at the balloon forming region. The material that may be employed as an adhesive or sizing agent is a bio-compatible material enumerated by an in vivo decomposable polymer, such as polylactic acid (PLA), water-soluble protein, such as gelatin, or fibrin sizing agent.

If, for example, PLA is dissolved as a solute in a solvent to give a solution which is coated on the stent and dried, the solution is left as a solid film to play the role of an adhesive. However, this method cannot be applied to the PLA stent because the PLA stent is dissolved in the solution. Thus it is necessary to employ some other bio-compatible material for the PLA stent.

Meanwhile, the bio-compatible material, used as the adhesive, may be applied to the stent in its entirety, or only to the overlapped region of the bioabsorbable polymer fibers.

EXPERIMENT 1

A yarn of polylactic acid fibers, admixed with barium sulfate, was meandered and applied to the peripheral surface of a tubular-shaped member to form a luminal stent. A plurality of such luminal stents, each being 4 mm in diameter and 20 mm in length, were applied to the coronary artery of a test animal, using a catheter fitted with a balloon. Observation by X-ray radiation revealed that the shape of the stent was maintained substantially unchanged for about 3 to 6 months and disappeared in about 6 to 12 months by being absorbed by the living tissue. During this period, inflammation or excess hypertrophy of the endothelial cells of the blood vessel was not observed.

EXPERIMENT 2

A yarn of polyglycol acid fibers, admixed with barium sulfate, was looped to be a plane-shaped and applied to the peripheral surface of a tubular-shaped member to form a luminal stent. A plurality of such luminal stents, each being 4 mm in diameter and 20 mm in length, were applied to the femoral artery of a test animal. Observation by X-ray radiation revealed that the shape of the stent was maintained substantially unchanged for about 2 to 6 weeks and absorbed by the living body in about 2 to 3 months. During this period, inflammation or excess hypertrophy of the endothelial cells of the blood vessel was not observed.

I claim:

1. A luminal stent formed from a single, continuous yarn of continuous bioabsorbable polymer fibers in a non-woven, non-knitted, and meandering state in a shape conforming to a tube.

2. The luminal stent as claimed in claim 1, characterized in that the bioabsorbable polymer is at least one selected from the group consisting of polylactic acid, polyglycol acid, polyglactin (polyglycol acid—polylactic acid copolymer), polydioxanone, polyglyconate (trimethylene carbonate—glycolide copolymer), and a copolymer of ε-caprolactone with polyglycol acid or polylactic acid.

3. The luminal stent as claimed in claim 1, characterized in that the bioabsorbable polymer fibers are non-circular in cross-section.

4. The luminal stent as claimed in claim 1, characterized in that the bioabsorbable polymer fibers present surface irregularities.

5. The luminal stent as claimed in claim 1, characterized in that at least one of an agent impermeable to X-rays, a carcinostatic agent and an anti-thrombotic agent is mixed into the bioabsorbable polymer fibers.

6. The luminal stent as claimed in claim 1, characterized in that at least one of an agent impermeable to X-rays, a carcinostatic agent, an anti-thrombotic agent and cells of a living body is deposited on the surface of the bioabsorbable polymer fibers.

7. The luminal stent as claimed in claim 1, characterized in that the bioabsorbable polymer fibers are hollow in cross-section.

8. A device for applying a luminal stent comprising:

a catheter having a balloon-forming portion at a distal end thereof; and a luminal stent formed from a single, continuous yarn of bioabsorbable polymer fibers in a non-woven, non-knitted and meandering state in a shape conforming to peripheral surface of a tube, said luminal stent being fitted over said balloon-forming portion.

9. The device for applying a luminal stent as claimed in claim 8, wherein the luminal stent is coated with a bio-compatible material and thereby affixed to the balloon-forming portion.

10. The device for applying a luminal stent as claimed in claim 9, characterized in that the bio-compatible material is at least one selected from an in vivo decomposable polymer, a water-soluble polymer, water-soluble protein and fibrin sizing agent.

11. The device for applying a luminal stent as claimed in claim 9, characterized in that the bio-compatible material is polylactic acid (PLA).

\* \* \* \* \*